US00PP15634P2

(12) United States Plant Patent
Bernuetz

(10) Patent No.: US PP15,634 P2
(45) Date of Patent: Mar. 8, 2005

(54) ***ARGYRANTHEMUM* PLANT NAMED 'OHAR01240'**

(50) Latin Name: *Argyranthemum×hybrida*
Varietal Denomination: OHAR01240

(75) Inventor: Andrew Bernuetz, Silverdale (AU)

(73) Assignee: Oasis Horticulutre, Pty. Ltd, Winmalee (AU)

( * ) Notice: Subject to any disclaimer, the term of this patent is extended or adjusted under 35 U.S.C. 154(b) by 47 days.

(21) Appl. No.: 10/741,780

(22) Filed: Dec. 19, 2003

(51) Int. Cl.[7] ..... A01H 5/00
(52) U.S. Cl. ..... Plt./263
(58) Field of Search ..... Plt./263

(56) References Cited

U.S. PATENT DOCUMENTS

PP13,541 P2 * 2/2003 Morgan ..... Plt./263
PP14,174 P2 * 9/2003 Cunneen ..... Plt./263

OTHER PUBLICATIONS

UPOV ROM GTITM Computer Database, GTI Jouve Retrieval Software 2004/02 Citation for 'OHAR01240'.*

* cited by examiner

*Primary Examiner*—Kent Bell
*Assistant Examiner*—W C Haas
(74) *Attorney, Agent, or Firm*—Wood, Phillips, Katz, Clark & Mortimer

(57) ABSTRACT

A new and distinct cultivar of *Argyranthemum* plant named 'OHAR01240', characterized by its single inflorescence form with pink-colored ray florets and yellow-colored disc florets, freely branching character, medium green-colored foliage and compact upright growth habit.

1 Drawing Sheet

Latin name of the genus and species of plant claimed: *Argyranthemum×hybrida.*
Variety denomination: 'OHAR01240'.

BACKGROUND OF THE INVENTION

The present invention relates to a new and distinct cultivar of *Argyranthemum* plant botanically known as *Argyranthemum×hybrida* and hereinafter referred to by the cultivar name 'OHAR01240'.

The *Argyranthemum* originated in a controlled breeding program in Winmalee, New South Wales, Australia during February 2001. The objectives of the breeding program were the development of *Argyranthemum* plants that are freely branching having a compact upright growth habit are freely flowering and have unique flower coloration.

The female (seed) parent of the new cultivar was the *Argyranthemum* cultivar 'Cobeer' (U.S. Plant Pat. No. 14,174) characterized by its fully double inflorescence form, pink-colored ray florets, compact growth habit, and dark green foliage. The male (pollen) parent of the new cultivar was the *Argyranthemum* cultivar 'Holly Belle', (not patented) characterized by its single inflorescence form, light pink-colored ray florets and medium growth habit. Seed from the above stated cross-pollination was germinated and grown to maturity. One plant from within the progeny was discovered and selected by the inventor during October 2001, in a controlled environment at Winmalee, New South Wales, Australia.

Asexual reproduction of the new cultivar by terminal stem cuttings taken since October 2001 at Winmalee, NSW, Australia and West Chicago, Ill. has demonstrated that the new cultivar reproduces true to type, with all the characteristics as herein described, firmly fixed and retained through successive generations of such asexual propagation.

SUMMARY OF THE INVENTION

The new cultivar has not been observed under all possible environmental conditions to date. Accordingly, it is possible that the phenotype may vary somewhat with variations in the environment, such as temperature, light intensity, and day length without, however, any variance in genotype.

It was repeatedly found that the cultivar of the present invention:

1. Exhibits a single inflorescence form with pink-colored ray florets and yellow-colored disc florets,
2. Forms medium green-colored foliage,
3. Exhibits a freely branching character, and
4. Exhibits a compact upright growth habit.

Plants of the new cultivar differ from plants of the female parent primarily in flower form and foliage color, and from plants of the male parent primarily in growth habit.

Plants of the new cultivar are most similar to the cultivar 'Cobsing' (U.S. Plant Pat. No. 13,541). However, in side-by-side comparisons, plants of the new cultivar differ from plants of 'Cobsing' in the following characteristics:

1. Plants of the new cultivar have flowers of a darker pink color then plants of 'Cobsing', and
2. Plants of the new cultivar have more ray florets per inflorescence than plants of 'Cobsing'.

Plants of the new cultivar have larger leaves than plants of 'Cobsing'.

BRIEF DESCRIPTION OF THE PHOTOGRAPHS

The accompanying photographs show as nearly true as it is reasonably possible to make the same in color illustrations of this type, typical flower and foliage characteristics of the new cultivar. Colors in the photographs differ slightly from the color values cited in the detailed description which more accurately describe the colors of the new cultivar. The plants were grown in 10 m cm pots for 10 weeks in a greenhouse at West Chicago, Ill.

DETAILED BOTANICAL DESCRIPTION

Figure 1:
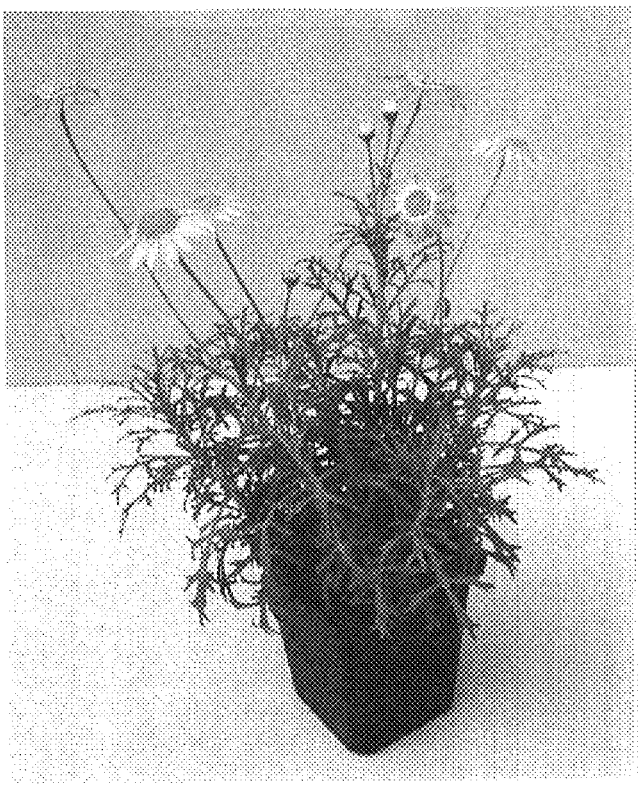
FIG. 1 illustrates a side view of the overall growth and flowering habit of the new cultivar.
Figure 2:
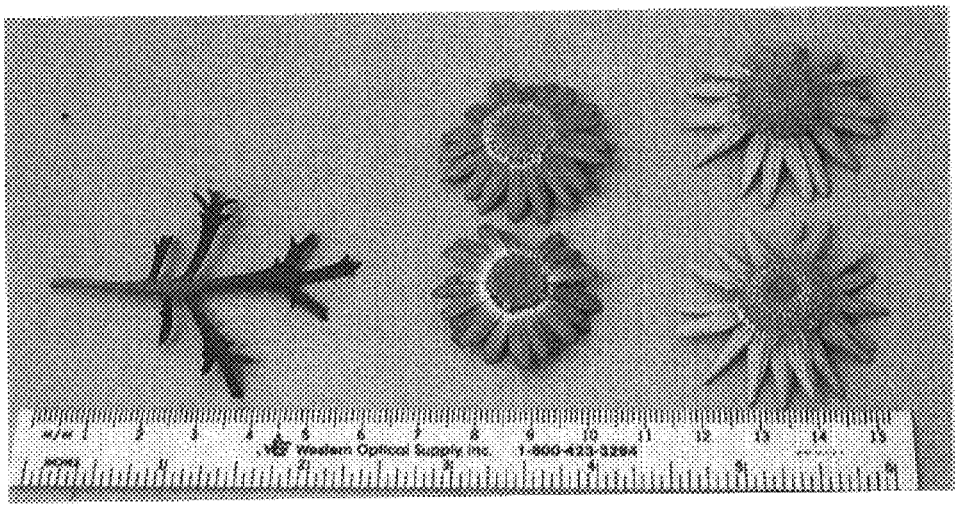
FIG. 2 illustrates a close-up view of a single leaf and four individual flowers showing the variation in flower color, ray floret shape and disc floret size and color from first opening (lower left) to fully open (lower right).

The chart used in the identification of colors described herein is The R.H.S. Colour Chart of The Royal Horticultural Society, London, England, 1995 edition, except where color terms of ordinary significance are used. The color values were determined on Sep. 25, 2003. The readings were taken between 1:00 and 3:00 p.m. under natural daylight conditions. The plants were produced from cuttings taken from stock plants and were grown in a double polycarbonate covered greenhouse in West Chicago, Ill. under conditions comparable to those used in commercial practice. The plants were grown utilizing a soilless growth medium. Greenhouse temperatures were maintained at approximately 65°–78° F. (18°–25° C.) during the day and approximately 50–60° F. (10°–15° C.) during the night. Greenhouse light levels were maintained at 6,000–9,000 footcandles during the day. Plants used for the following descriptions and measurements were grown in 10 cm pots for 10 weeks from rooted cuttings.

Botanical classification: *Argyranthemum×hybrida* 'OHAR01240'

Parentage:

*Female (seed) parent.*—*Argyranthemum* cultivar 'Cobeer' (U.S. Plant Pat. No. 14,174).

*Male (pollen) parent.*—*Argyranthemum* cultivar 'Holly Belle' (not patented)

Propagation:

*Type cutting.*—Terminal stem.

*Time to initiate roots.*—Approximately 7 to 10 days.

*Time to produce a rooted cutting.*—Approximately 14 to 21 days.

*Root description.*—Fine fibrous,

*Rooting habit.*—Freely branching.

Plant description:

*Crop time.*—Approximately 8 weeks in a 10 cm pot.

*Habit of growth.*—Compact. Freely branching. One or two pinches improves basal branching.

*Form.*—Upright, mounded.

*Plant height.*—A mature plant, 10 weeks after the planting of a rooted cutting, commonly measures approximately 25 cm from soil level to top of plant plane.

*Plant width (area of spread).*—Approximately 30 cm.

*Branch description.*—Quantity per plant: Approximately 9. Texture: Glabrous. Length from soil level to base of peduncle: Approximately 19 cm. Diameter: Approximately 4 mm. Internode length at middle of branch: Approximately 9 mm. Color: 145A.

*Foliage description.*—Leaves are simple and non-fragrant. Arrangement: Alternate. Quantity per branch: Approximately 25. Aspect: At an acute angle to the stem. Shape: Pinnatifed. Margin: Entire. Apex: Acute. Base: Sessile, clasping. Texture: Upper and lower surfaces are glabrous. Venation pattern: Pinnate. Length: Approximately 6.7 cm. Width: Approximately 4.5 cm. Color of mature foliage. Upper surface: 137A with venation of 144B. Lower surface: Slightly more yellow than 137C with venation of 144B.

Flowering description:

*Flowering habit.*—Freely flowering.

*Natural flowering season.*—Year round in greenhouse environment and spring through autumn in outdoor garden.

Inflorescence description:

*Appearance.*—Solitary, composite. Persistent. Shape: Round. Aspect: Facing upward or outward. Disc and ray florets develop acropetally on a capitulum. Fragrance: None. Quantity of flowers and buds per plant: Approximately 37.

*Size.*—Diameter: Approximately 3.1 cm. Depth: Approximately 9 mm.

*Lastingness of inflorescence.*—Approximately 7–10 days.

*Bud.*—Shape: Round, flat. Diameter: Approximately 7 mm. Depth: Approximately 6 mm. Color: 165B.

*Ray florets.*—Quantity per inflorescence: Approximately 21, arranged in a single whorl. Aspect: Flat to slightly concave. Arrangement: Very slightly overlapping. Shape: Ligulate. Margin: Entire. Apex: Emarginate. Base: Attenuate and fused to form tube. Texture: Glabrous and ribbed. Length: Approximately 1.4 cm. Width: Approximately 3 mm. Color when opening. Upper and lower surfaces: N74C with 155D at base. Color when fully open: Upper and lower surface: Gradually changes from 75C at tip to N74D near base with base of 155D. Tube texture: Pubescent. Tube color: 154C.

*Disc.*—Diameter: Approximately 1.5 cm. Depth: Approximately 7 mm.

*Disc florets.*—Quantity per inflorescence: Approximately 173. Shape: Tubular with five lobes each having an acute apex. Margin: Entire. Texture: Glabrous. Length: Approximately 5 mm. Diameter at apex: Approximately 1 mm. Diameter at base: Approximately 0.5 mm. Color 13A, translucent. Calyx: Shape: Tubular. Length: approximately 2 mm. Diameter: 1 mm. Color: Colorless, translucent.

*Phyllaries.*—Quantity per inflorescence: Approximately 26. Arrangement: Imbricate, arranged in several rows. Shape: Ovate. Apex: Acute. Base: Truncate. Margin: Entire. Texture: Glabrous. Length: Approximately 5 mm. Width: Approximately 4 mm. Color of upper surface: Closest to 145C. Color of lower surface: Closest to 145D.

*Peduncle.*—Strength: Strong. Texture: Glabrous. Aspect: At an acute angle to the stem. Length: Approximately 8 cm. Diameter: Approximately 2 mm. Color: 144B.

*Reproductive organs.*—Androecium: Present on disc florets only. Stamens: 5 fused to form tube around pistil. Anther shape: Linear. Anther length: Approximately 1 mm. Anther color: 12B. Amount of pollen: Abundant. Pollen color: 14B. Gynoecium: Present on ray and disc florets. There is one pistil per floret. Pistil length: 6 mm. Stigma shape: two parted. Stigma length: 0.7 mm. Stigma color: 1C. Style length: 3 mm. Style color: 144D. Ovary diameter. Less than 1 mm. Ovary color: 144C.

Seed and fruit production: Neither seed nor fruit production has been observed.

Disease and pest resistance: Resistance to pathogens and pests common to *Argyranthemums* has not been observed.

Hardiness zone: 'OHAR01240' is hardy in zones nine (9) and above.

What is claimed:

1. A new and distinct cultivar of *Argyranthemum* plant named 'OHAR01240' substantially as herein shown and described, which:

1. Exhibits a single inflorescence form with pink-colored ray florets and yellow-colored disc florets,
2. Forms medium green-colored foliage,
3. Exhibits a freely branching character, and
4. Exhibits a compact upright growth habit.

* * * * *